(12) United States Patent
Kirwan et al.

(10) Patent No.: US 8,460,388 B2
(45) Date of Patent: Jun. 11, 2013

(54) SPINAL INTERBODY DEVICE

(75) Inventors: John M. Kirwan, Wilbraham, MA (US);
R. Quinn Brown, Collierville, TN (US);
Hubert W. Pfabe, East Longmeadow, MA (US)

(73) Assignee: Incite Innovation LLC, Springfield, MA (US)

( * ) Notice: Subject to any disclaimer, the term of this patent is extended or adjusted under 35 U.S.C. 154(b) by 115 days.

(21) Appl. No.: 13/284,214

(22) Filed: Oct. 28, 2011

(65) Prior Publication Data

US 2013/0110242 A1 May 2, 2013

(51) Int. Cl.
*A61F 2/44* (2006.01)

(52) U.S. Cl.
USPC .................. 623/17.16; 623/17.11

(58) Field of Classification Search
USPC .......................... 623/17.11–17.16
See application file for complete search history.

(56) References Cited

U.S. PATENT DOCUMENTS

| | | |
|---|---|---|
| 4,904,261 A | 2/1990 | Dove et al. |
| 4,955,908 A | 9/1990 | Frey et al. |
| 5,397,364 A | 3/1995 | Kozak et al. |
| 5,571,109 A | 11/1996 | Bertagnoli |
| 5,800,547 A | 9/1998 | Schafer et al. |
| 5,800,550 A | 9/1998 | Sertich |
| 5,888,223 A | 3/1999 | Bray, Jr. |
| 5,976,139 A | 11/1999 | Bramlet |
| 6,077,264 A | 6/2000 | Chemello |
| 6,096,080 A | 8/2000 | Nicholson et al. |
| 6,102,950 A * | 8/2000 | Vaccaro ............. 623/17.16 |
| 6,156,037 A | 12/2000 | LeHuec et al. |
| 6,179,873 B1 | 1/2001 | Zientek |
| 6,183,474 B1 | 2/2001 | Bramlet et al. |
| 6,193,757 B1 | 2/2001 | Foley et al. |
| 6,235,059 B1 | 5/2001 | Benezech et al. |
| 6,241,769 B1 | 6/2001 | Nicholson et al. |

(Continued)

FOREIGN PATENT DOCUMENTS

| | | |
|---|---|---|
| EP | 0697200 | 2/1996 |
| FR | 2835179 | 8/2003 |

(Continued)

OTHER PUBLICATIONS

International Preliminary Report on Patentability mailed Jul. 26, 2011 for International Application No. PCT/US2010/020969.

(Continued)

*Primary Examiner* — Kevin T Truong
*Assistant Examiner* — Christian Sevilla
(74) *Attorney, Agent, or Firm* — Cantor Colburn LLP

(57) ABSTRACT

A spinal interbody device is provided having a cage and an anchor. The cage includes a center portion with a first surface and a second surface. A first arm and a second arm extend from the center portion with the first arm having a pair of first projections and the second arm having a pair of second projections. The pair of first projections and the pair of second projections are disposed on opposing sides of an open side. The anchor includes a blade that is movable between a first position and a second position. The blade is disposed to engage the first surface and deflect as the anchor is moved from the first position to the second position. Wherein the blade is at least partially disposed between one of the pair of first projections and the center portion when the anchor is in the second position.

14 Claims, 23 Drawing Sheets

U.S. PATENT DOCUMENTS

| | | |
|---|---|---|
| 6,432,106 B1 | 8/2002 | Fraser |
| 6,443,954 B1 | 9/2002 | Bramlet et al. |
| 6,447,546 B1 * | 9/2002 | Bramlet et al. ............ 623/17.16 |
| 6,461,359 B1 | 10/2002 | Tribus et al. |
| 6,471,724 B2 | 10/2002 | Zdeblick et al. |
| 6,558,423 B1 | 5/2003 | Michelson |
| 6,579,290 B1 | 6/2003 | Hardcastle et al. |
| 6,695,851 B2 | 2/2004 | Zdeblick et al. |
| 6,716,245 B2 | 4/2004 | Pasquet et al. |
| 6,743,256 B2 | 6/2004 | Mason |
| 6,800,093 B2 | 10/2004 | Nicholson et al. |
| 6,805,714 B2 | 10/2004 | Sutcliffe |
| 6,890,355 B2 | 5/2005 | Michelson |
| 6,972,019 B2 | 12/2005 | Michelson |
| 6,984,234 B2 | 1/2006 | Bray |
| 7,018,414 B2 | 3/2006 | Brau et al. |
| 7,041,135 B2 | 5/2006 | Michelson |
| 7,077,864 B2 | 7/2006 | Byrd, III et al. |
| 7,135,024 B2 | 11/2006 | Cook et al. |
| 7,163,560 B2 | 1/2007 | Mason |
| 7,163,561 B2 | 1/2007 | Michelson |
| 7,166,110 B2 | 1/2007 | Yundt |
| 7,172,627 B2 | 2/2007 | Fiere et al. |
| 7,232,464 B2 | 6/2007 | Mathieu et al. |
| 7,291,170 B2 | 11/2007 | Huppert |
| 7,297,162 B2 | 11/2007 | Mujwid |
| 2003/0199983 A1 | 10/2003 | Michelson |
| 2004/0249466 A1 | 12/2004 | Liu et al. |
| 2005/0055027 A1 | 3/2005 | Yeung et al. |
| 2006/0030851 A1 | 2/2006 | Bray et al. |
| 2006/0173543 A1 | 8/2006 | Brau et al. |
| 2006/0206208 A1 | 9/2006 | Michelson |
| 2006/0241621 A1 | 10/2006 | Moskowitz et al. |
| 2006/0253201 A1 | 11/2006 | McLuen |
| 2007/0049943 A1 | 3/2007 | Moskowitz et al. |
| 2007/0100452 A1 | 5/2007 | Prosser |
| 2007/0106384 A1 | 5/2007 | Bray et al. |
| 2007/0106388 A1 | 5/2007 | Michelson |
| 2007/0233253 A1 | 10/2007 | Bray et al. |
| 2007/0250167 A1 | 10/2007 | Bray et al. |
| 2007/0276377 A1 | 11/2007 | Yundt |
| 2008/0039846 A1 | 2/2008 | Lee et al. |
| 2009/0105832 A1 | 4/2009 | Allain et al. |
| 2009/0265007 A1 | 10/2009 | Colleran |
| 2010/0185289 A1 * | 7/2010 | Kirwan et al. ............ 623/17.11 |
| 2011/0035007 A1 | 2/2011 | Patel et al. |
| 2011/0230971 A1 | 9/2011 | Donner et al. |
| 2012/0078371 A1 | 3/2012 | Gamache et al. |

FOREIGN PATENT DOCUMENTS

| | | |
|---|---|---|
| WO | 9966867 | 12/1999 |
| WO | 2004080356 | 9/2004 |
| WO | 2008149223 A2 | 12/2008 |

OTHER PUBLICATIONS

International Search Report mailed Sep. 27, 2010 for PCT Application No. PCT/US2010/020969 filed Jan. 14, 2010; references cited in search report are listed above.

Written Opinion of the International Searching Authority mailed Sep. 27, 2010 for Application PCT/US2010/020969 filed Jan. 14, 2010.

International Search Report mailed Mar. 25, 2013 for International Application Serial No. PCT/US2012/057764; International filing date Sep. 28, 2012. All references cited incorporated herein.

Written Opinion mailed Mar. 25, 2013 for International Application Serial No. PCT/US2012/057764; International filing date Sep. 28, 2012. All references cited incorporated herein.

* cited by examiner

SPINAL INTERBODY DEVICE

BACKGROUND OF THE INVENTION

The subject matter disclosed herein relates to an spinal interbody device, such as that used in lumbar or cervical spine procedures for example, and in particular relates to a stand-alone spinal interbody device having a fixation system.

Spinal interbody devices are common in spine procedures today. These devices encompass many products in the marketplace. Implants are constructed from PEEK, titanium and various other materials and have been designed for insertion through anterior, posterior and lateral approaches. Typically, interbody devices require additional fixation to create a fusion across the intended vertebral level. In lumbar surgery, this supplemental fixation can include an anterior plate or pedicle screws and rods inserted posteriorly in a 360° procedure. Studies have shown that interbody devices have poor outcomes when they are not combined with a method of fixation.

One type of spinal interbody device is called a stand-alone. This type of implant consists of an interbody device and a means of fixation all in one. Typically this fixation has been accomplished using screws that are placed through the implant and fixed at oblique angles to the adjacent superior and inferior vertebrae. This method requires considerable access due to the extreme angle of insertion for the screws.

While existing spinal interbody devices are suitable for their intended purposes, improvements may be made. In particular, it is desirable to have a stand-alone spinal interbody device with an integrated fixation system that may be readily implanted while reducing the access space needed by a surgeon during a spinal procedure.

BRIEF DESCRIPTION OF THE INVENTION

According to one aspect of the invention, a spinal interbody device is provided. The device includes a cage having a center portion with at least one surface. An anchor having at least one blade is provided and is movable between a first position and a second position. The at least one blade is disposed to engage the at least one surface and deform as the anchor is moved from the first position to the second position. A locking means for coupling the anchor to the cage.

According to another aspect of the invention, a spinal interbody device is provided. The device includes a cage having a first member coupled to a second member. The first member has a center portion with a first arm and a second arm extending from opposing ends, the center portion further having a first surface and a second surface. The first arm has at least one first projection on an end opposite the center portion and the second arm having at least one second projection an end opposite the center portion, the first arm and second arm defining an open side. An anchor is provided having a body with at least one blade extending from one side, the anchor being movable between a first position and a second position. The at least one blade is disposed to contact the first surface when the anchor is moved from the first position to the second position, wherein the at least one blade is at least partially disposed between the at least one first projection and the center portion when the anchor is in the second position.

According to yet another aspect of the invention, a spinal interbody device is provided having a cage. The cage includes a first contact surface and a second contact surface. The cage further includes a first portion and a second portion arranged substantially parallel with the first portion. A third portion is disposed between the first portion and the second portion, the third portion having at least one surface thereon, the third portion having a first opening extending therethrough, the first opening being substantially parallel to the first portion. An anchor is provided having at least one arm arranged to removably couple with the first opening. The anchor further having at least one blade arranged to engage the at least one surface as the at least one arm is moved toward the first opening, wherein the at least one blade cooperates with the at least one surface to deform the at least one blade past the first contact surface when the at least one arm is coupled to the first opening.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION OF THE INVENTION

Figure 21:
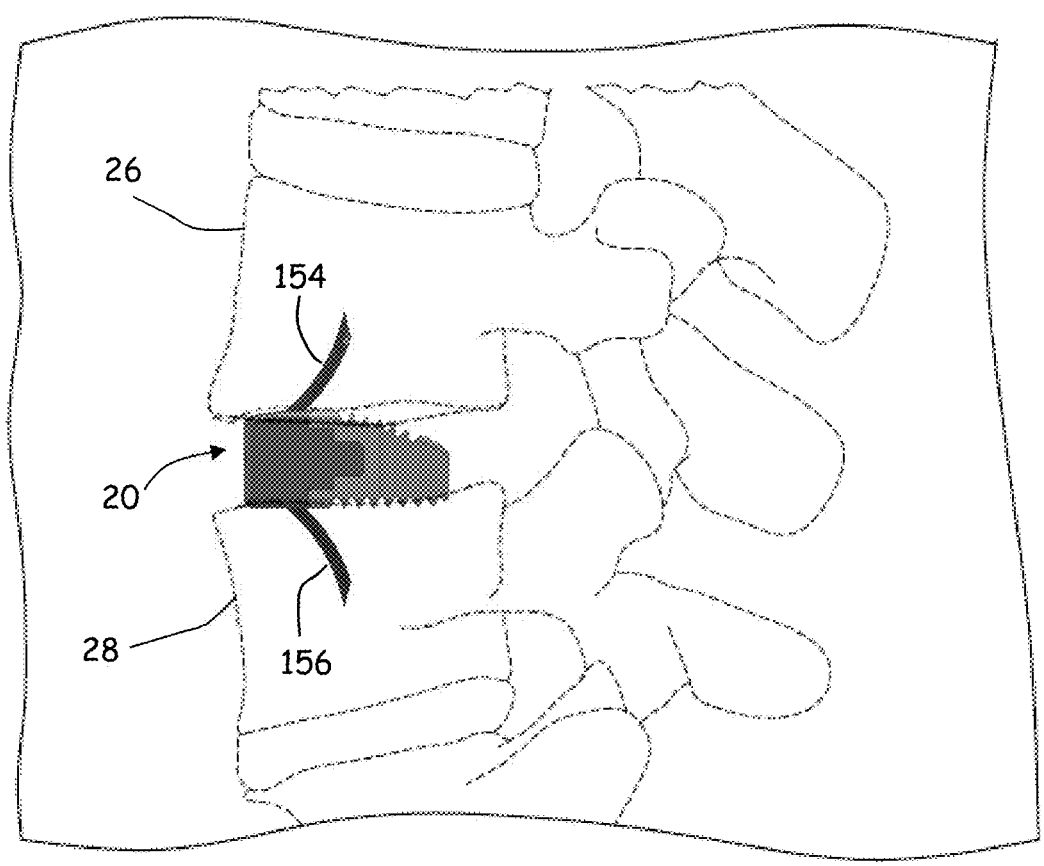
FIG. 21 is a side view with the superior vertebrae and the inferior vertebrae illustrated in phantom line of the spinal interbody device of FIG. 19.

Referring to FIGS. 1-8, an embodiment of a spinal interbody device 20 is shown. The device 20 includes a cage 22 and a fixation device, such as anchor 24. The cage 22 can be used alone with supplemental fixation, such as rods and screws or a plate for example, or with the included anchor 24, thereby providing a stand-alone design. The cage 22, can be constructed of various biocompatible materials including, but not limited to, titanium or a polymer such as polyetheretherketone (PEEK) for example. With the anchor 24 in place, the spinal interbody device 20 would be placed between the adjacent vertebrae after the partial or complete disc removal as illustrated in FIG. 21. As will be discussed in more detail below, once the cage 22 is in place within the patient, the anchor 24 would be deployed to couple the cage 22 into the adjacent superior and inferior vertebral bodies 26, 28 (FIG. 21), thereby securing the implant in place. Thus the spinal interbody device 20 provides advantages in that supplemental fixation, such as pedicle screws and rods or an anterior plate for example, and its associated increased surgical time, is obviated. Further, the cage 22 may include an optional opening 30 that may be used for autograft or alternative biomaterials to facilitate bone in-growth. The surgeon may utilize a tool or tools to facilitate the insertion of the spinal interbody device 20 to both place the spinal interbody device 20 and provide a means for deployment of the anchor 24.

It should be appreciated that while the cage 22 is illustrated with the opening 30, this is for exemplary purposes and the claimed invention should not be so limited. For example, in different applications, it may be desirable to have the cage 32 be substantially solid for example. While the embodiments herein discusses the spinal procedures with respect to an anterior insertion approach, the claimed invention may also be used in other spinal procedures, such as but not limited to posterior insertion and lateral insertion for example.

As used herein the term "anterior" refers to the front side from the perspective of the patient, while the term "posterior" refers the backside from the perspective of the patient. Further, as used herein, the term "superior" means closer to the head of the patient and "inferior" means closer to the feet of the patient.

The cage 22 is a member sized and shaped to tightly fit between vertebrae. The cage 22 may taper from the anterior side 32 to the posterior side 34 to match patient anatomy. The cage 22 may also have a curved top contact surface 36 and a substantially flat bottom contact surface 38. In one embodiment, the top contact surface 36 and bottom contact surface 38 include a plurality of optional teeth or grooves 40 that engage the adjacent superior and inferior vertebrae to assist in maintaining the spinal interbody device 20 in place.

It should be appreciated that the curvature, taper, or angle between the contact surfaces 36, 38 may be varied to match the patient anatomy. The height, or distance between the contact surfaces 36, 38 may also be changed to match the patient anatomy. Further, while the contact surfaces 36, 38 are illustrated as being substantially flat on one side and curved on the other, other profiles may be used, including but not limited to parallel, tapered, concave or convex surfaces for example. Additionally, the cage 22 may be substantially cylindrical, such as that shown in U.S. Pat. No. 5,782,919, which is incorporated by reference in its entirety.

In the one embodiment, the cage 22 is a generally U-shaped body having a first portion 42 and a second portion 44 connected on the posterior side 34 by a wall 46. A center portion 48 interconnects the first portion 42 and the second portion 44 to define the opening 30. The center portion 48 is offset from the anterior side 32 to define an area with an open side 50. As will be discussed in more detail below, the center portion 48 is offset a sufficient distance, and the open side 50 is sized, to receive the anchor 24 when in the deployed position.

Figure 9:
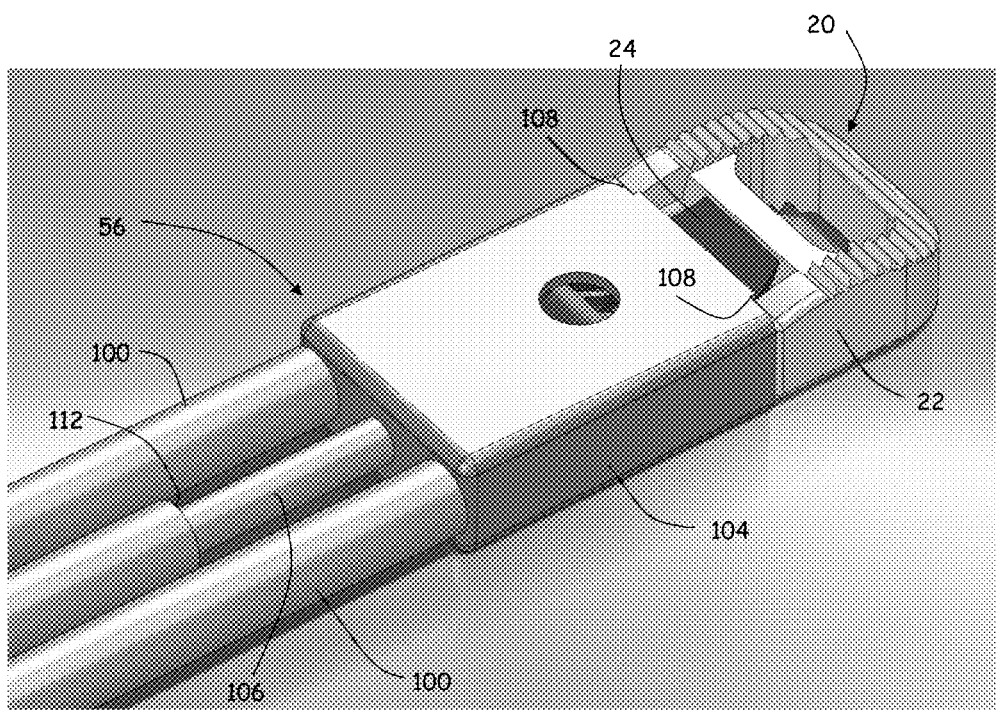
FIG. 9 is a perspective view of the spinal interbody device of FIG. 5 coupled to a surgical tool.
Figure 10:
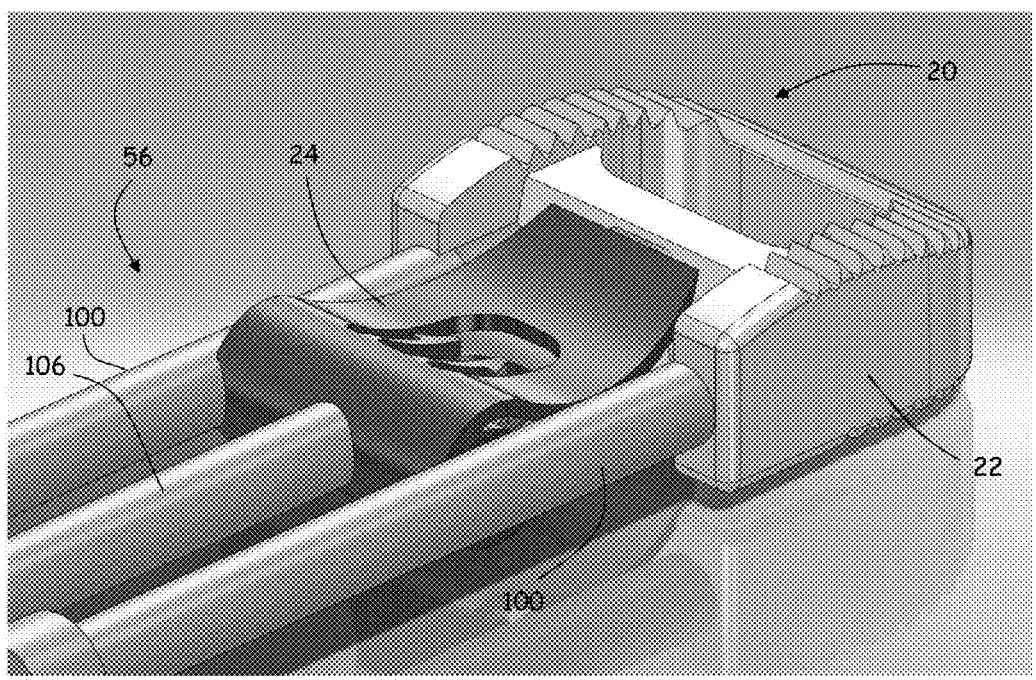
FIG. 10 is a perspective view of the spinal interbody device of FIG. 9 with a surgical tool housing removed.
Figure 11:
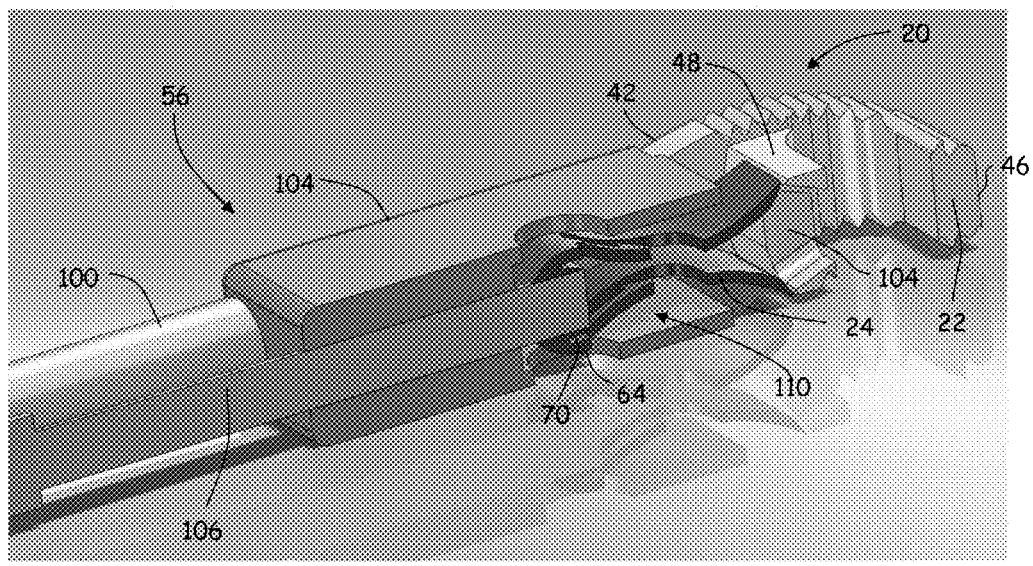
FIG. 11 is a perspective sectional view of the spinal interbody device of FIG. 9.
Figure 12:
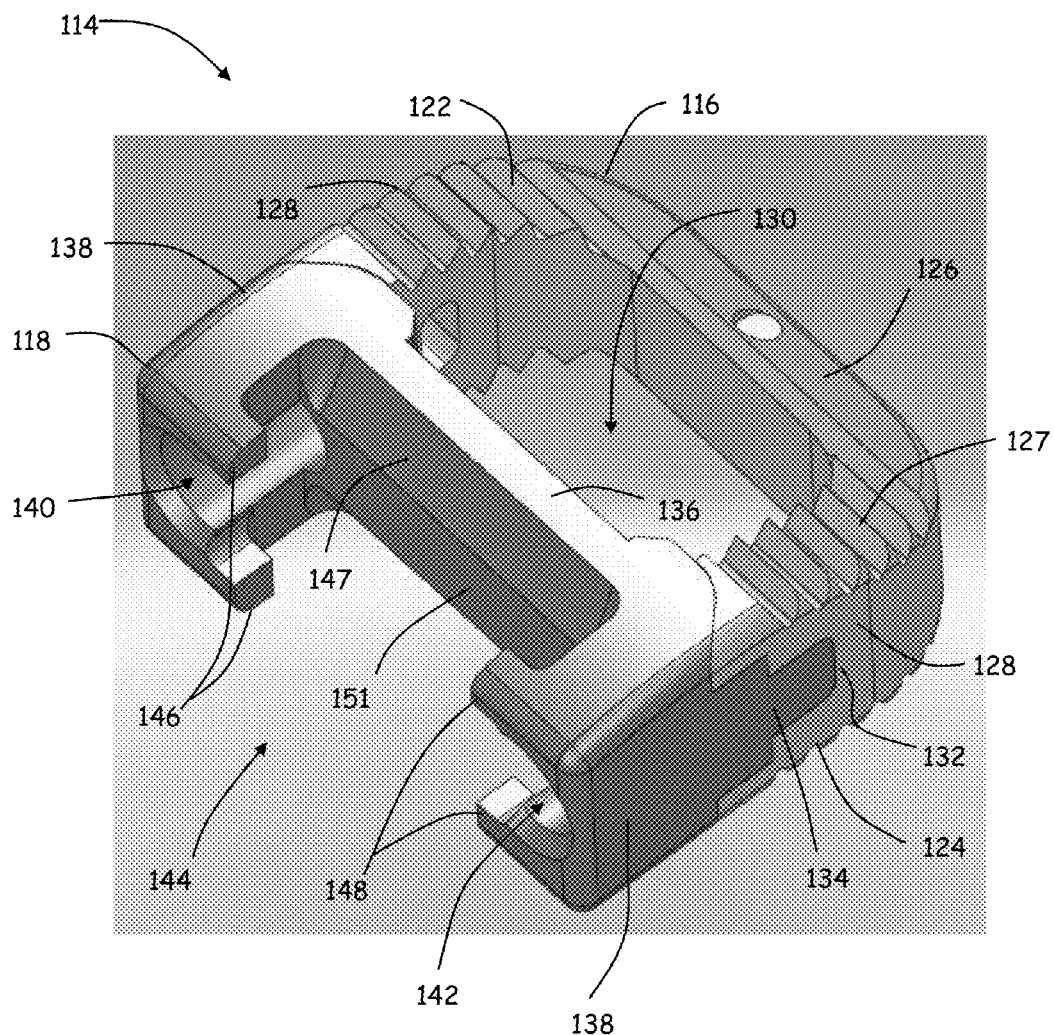
FIG. 12 is a perspective view of a cage for a spinal interbody device in accordance with another embodiment of the invention.
Figure 13:
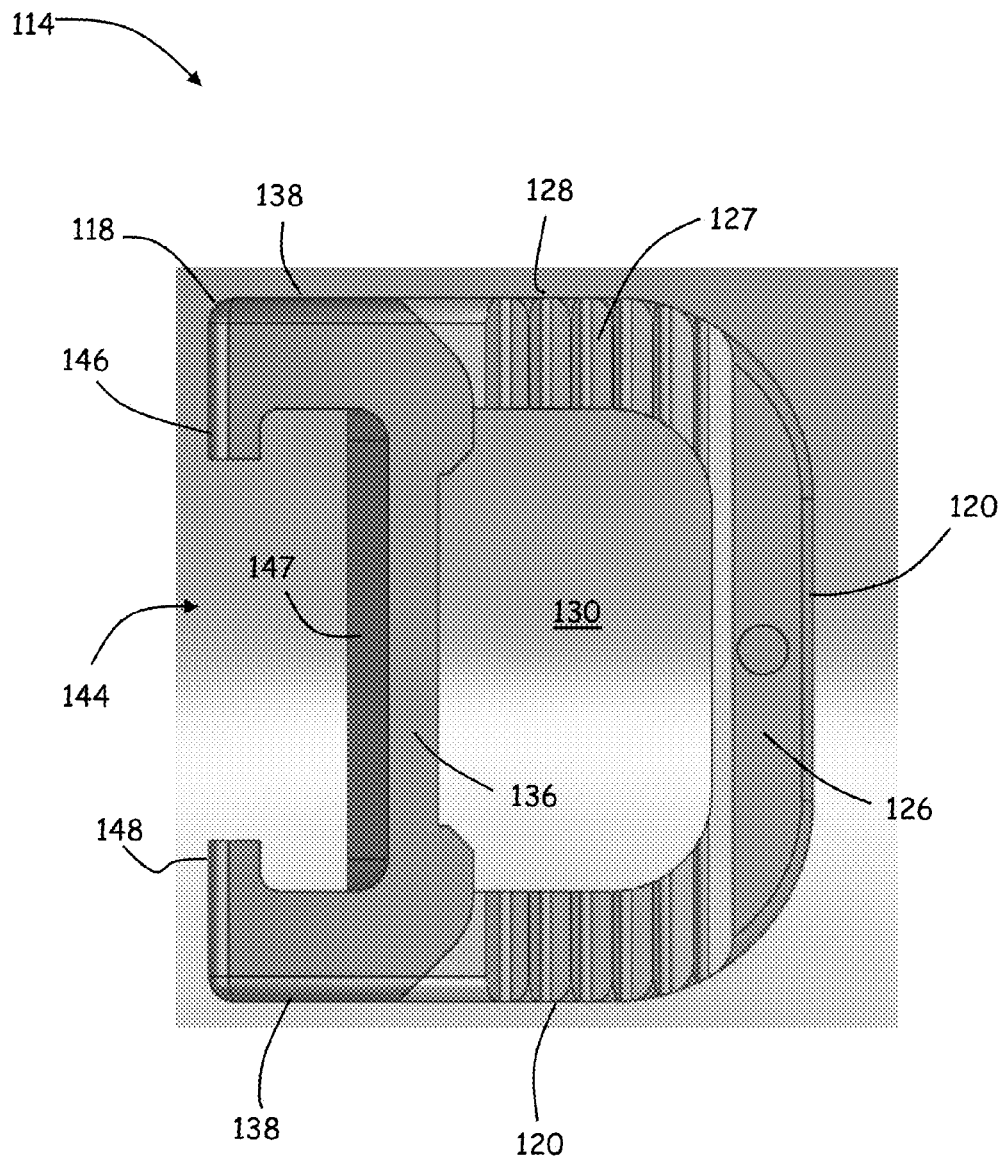
FIG. 13 is a top view of the cage of FIG. 12.
Figure 14:
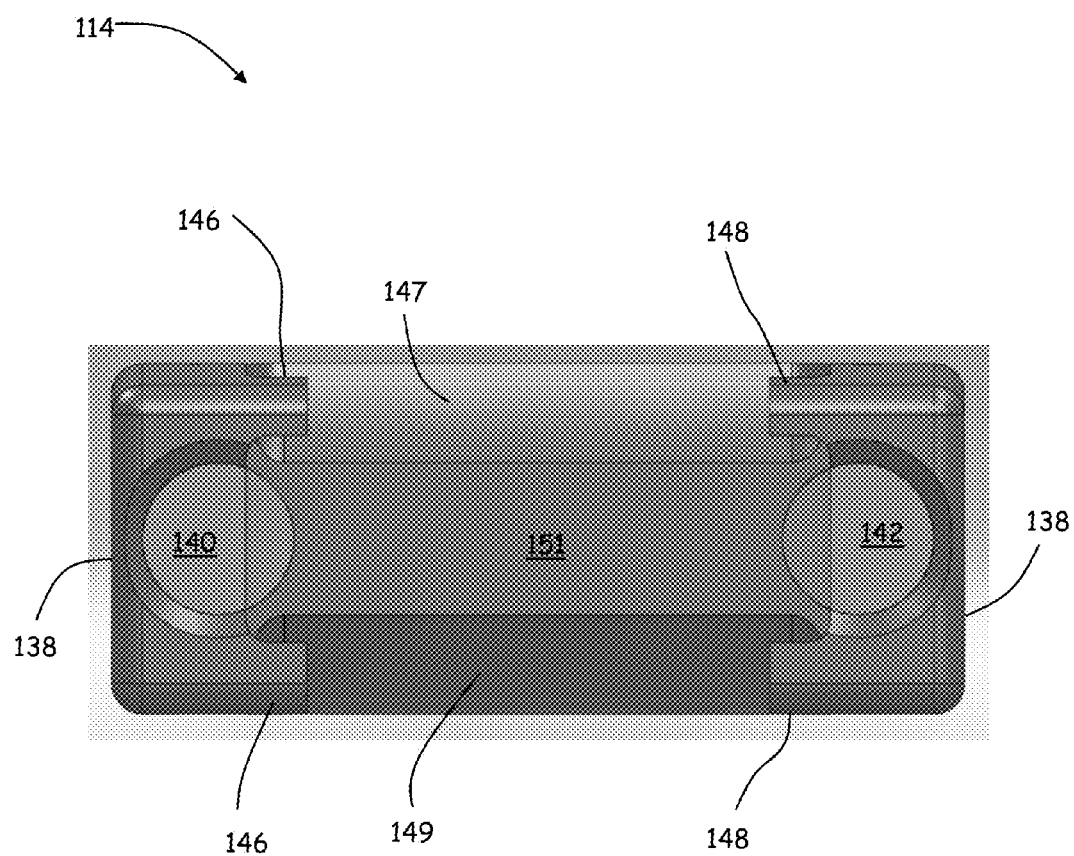
FIG. 14 is an anterior view of the cage of FIG. 12.

The first portion 42 and the second portion 44 each include an opening 52, 54 adjacent the open side 50. The openings 52, 54 may have threaded portions that allow the cage 22 to be coupled with a tool 56 (FIGS. 9-11). In one embodiment, the openings 52, 54 intersect with the open area adjacent the open side 50. It should be appreciated that this allows the device 20 to be smaller, such as for use in cervical spine procedures for example. In other embodiments, such as with a lumbar spinal procedure, the cage 22 may be larger and the openings 52, 54 may be completely enclosed by the first portion 42 and the second portion 44.

The center portion 48 includes a first surface 58 and a second surface 60. As will be discussed in more detail below, the first ramp surface 58 and second ramp surface 60 are angled to deflect a blade portion of the anchor 24 into the adjacent vertebrae. In one embodiment, the surfaces 58, 60 are disposed at 75 degrees relative to a horizontal plane extending through the center of the cage 22 (e.g. parallel to the bottom contact surface 38). In one embodiment, the surfaces 58, 60 are substantially mirror images of each other on opposing sides of the horizontal plane. The center portion 48 further includes an opening 62. In one embodiment, the opening 62 is a generally rectangular opening that tapers such that the area of the opening adjacent the surfaces 58, 60 is larger than the distal end.

Figure 1:
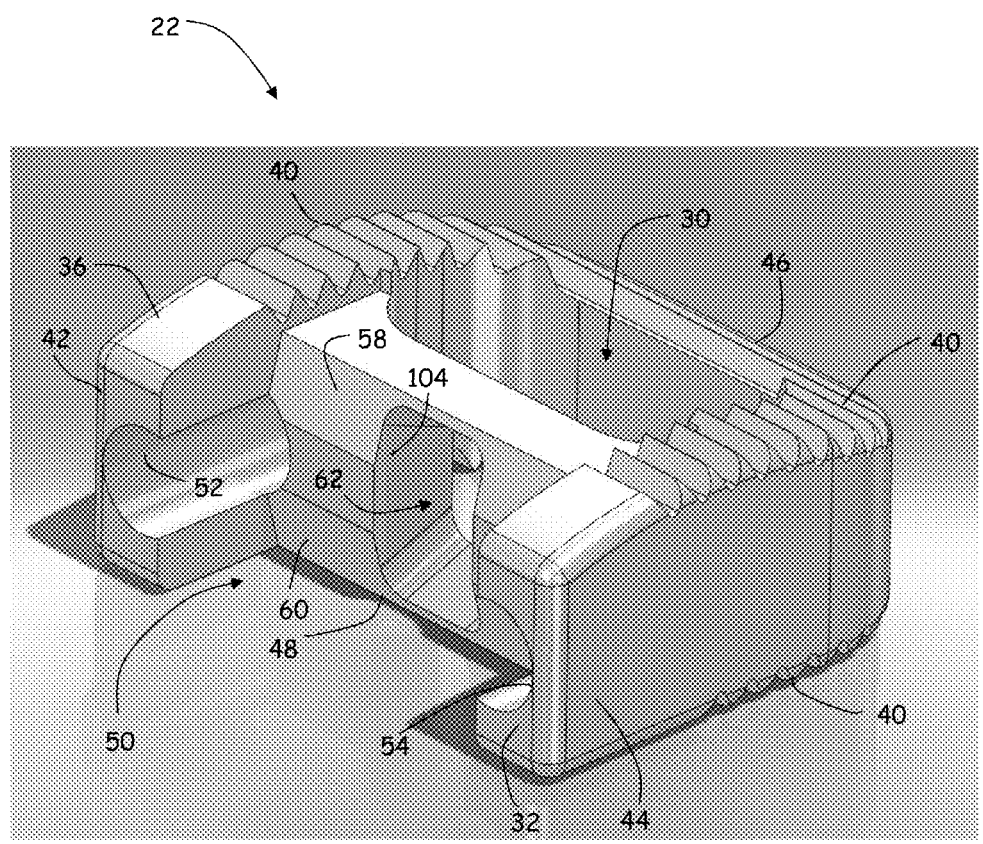
FIG. 1 is a perspective view of a cage for a spinal interbody device in accordance with an embodiment of the invention.
Figure 2:
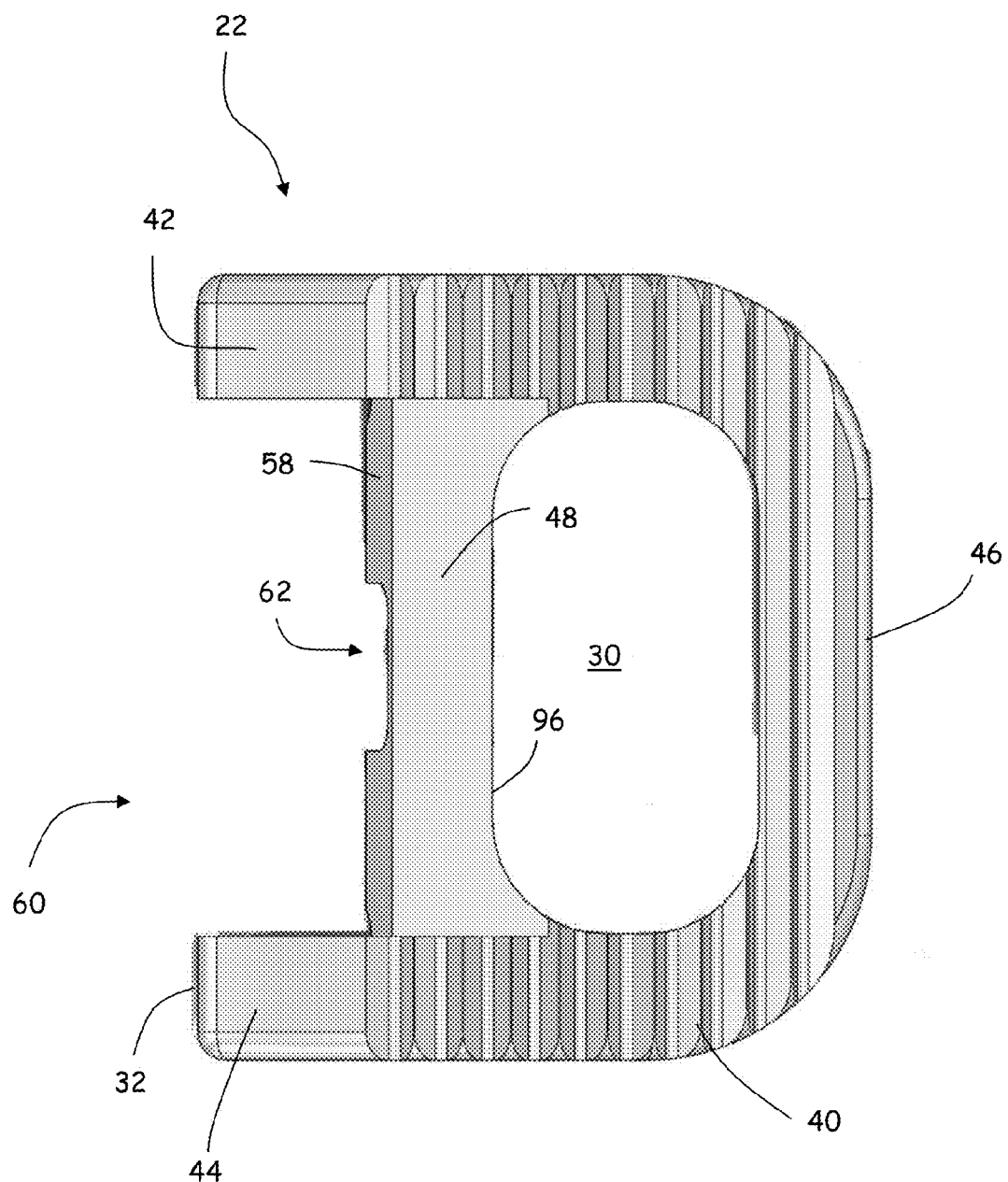
FIG. 2 is a top view of the cage of FIG. 1.
Figure 3:
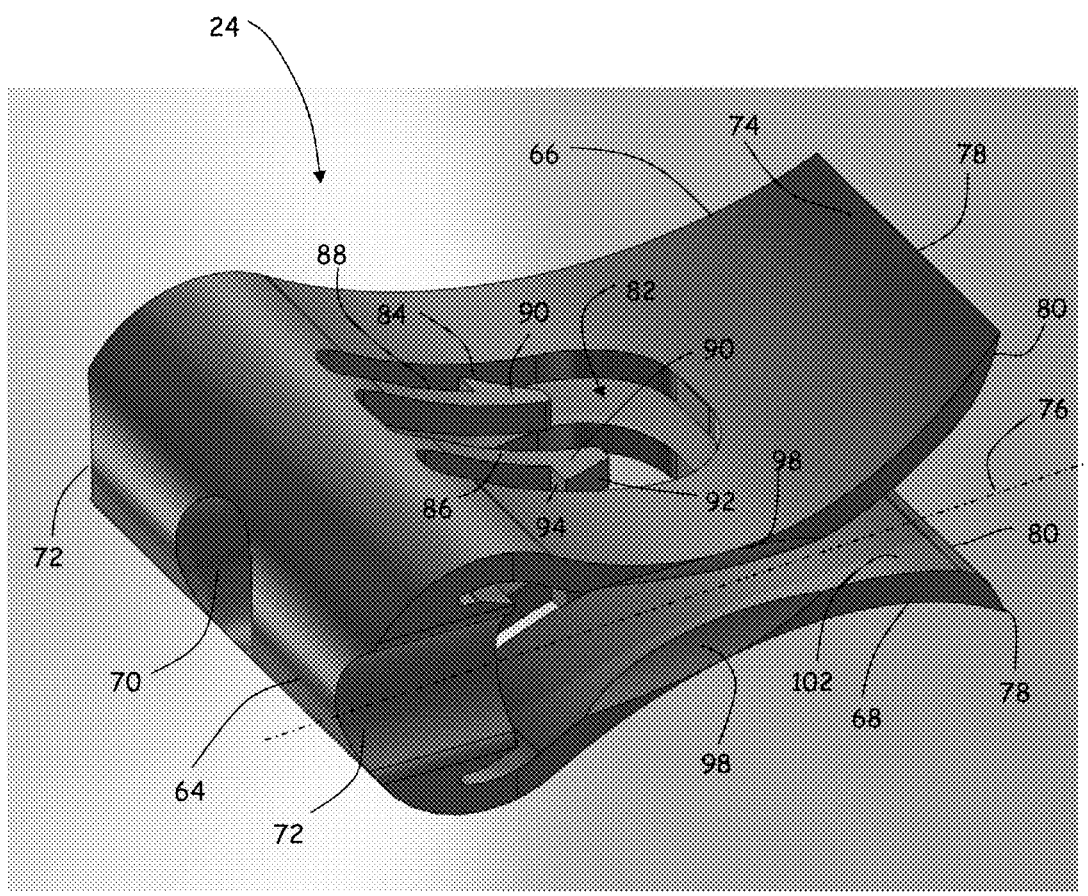
FIG. 3 is a perspective view of an anchor for use with the cage of FIG. 1.
Figure 4:
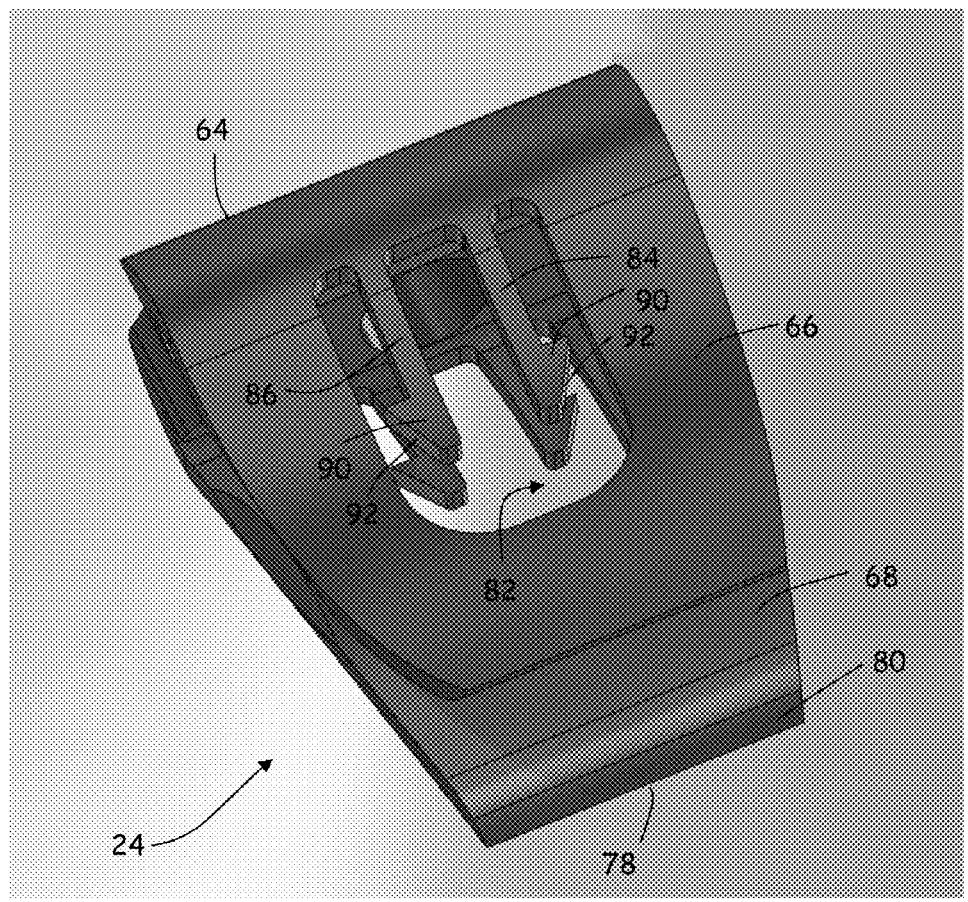
FIG. 4 is another perspective view of the anchor of FIG. 3.
Figure 5:
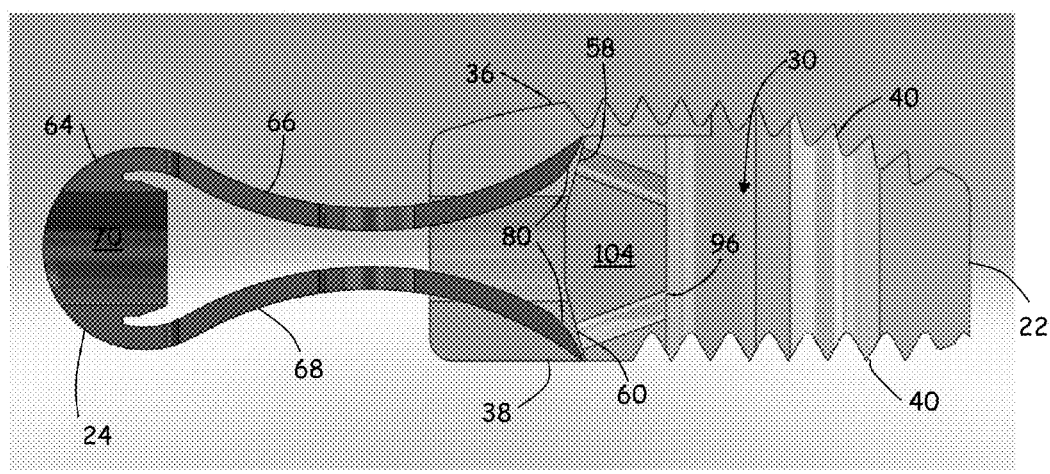
FIG. 5 is a side sectional view of a spinal interbody device in a first position.

An embodiment of an anchor 24 is shown in FIGS. 3-4. The anchor 24 includes a body 64 having a first blade 66 and a second blade 68 extending from one side. In one embodiment, the body 64 has a semi-cylindrical shaped anterior side. The anchor 24 may be made from a metal such as stainless steel or titanium for example. The body 64 is sized to be received within the open side 50 of the cage 22. The body 64 may include a threaded opening 70 located centrally along the width of the body 62. As will be discussed in more detail below, the threaded opening 70 allows the anchor 24 to be coupled to a tool for insertion or removal of the anchor 24 from a patient. In one embodiment, the body 64 includes a pair of semi-cylindrical slots 72 disposed on each end. The slots 72 are sized and positioned to allow one or more rods 100 (FIG. 10) from the tool 56 to extend past the anchor 24 into the cage 22.

Each of the blades 66, 68 is generally curved along the length of the blade and may also be tapered such that the distal end 47 of the blades 66, 68 are narrower than the end adjacent the body 64. The blades 66, 68 may also have a generally uniform thickness. In some embodiments, the curvature of the blades 66, 68 may not be constant and the curvature may change along the length of the blade 66, 68. The curvature of the blades 66, 68 is arranged such that the distal end 47 is curved away from a centerline 76. The distal end 74 may include an edge 78 that facilitates the insertion of the blades 66, 68 into the vertebrae. As will be discussed in more detail below, a surface 80 adjacent the edge 78 engages the surfaces 58, 60 allowing the blades 66, 68 to slide past and extend away from the cage 22. In one embodiment, the blades may include a semi-cylindrical surface 98 disposed along each side between the body 64 and the edge 78. The semi-cylindrical surfaces 98 are disposed co-axially with the slots 72 to provide clearance for rods 100 when the anchor 24 is coupled to the tool 56.

Each blade 66, 68 includes an opening 82 that extends through the thickness of the blade 66, 68 adjacent the body 64. Disposed within the opening 82 is at least one arm 84. In one embodiment, the anchor 24 has two arms 84, 86 extending from the body 64 within the opening 82. Each arm 84, 86 has a generally narrow body portion 88 with a head portion 90 on a distal end from the body 64. The head portion 90 includes an angled surface 92 that extends transverse to the surface of the blades 66, 68. Adjacent the angled surface 92 is a latching surface 94 that extends between the angled surface 92 and the body portion 88. As will be discussed in more detail herein, the arms 84, 86 form a locking means for coupling the anchor 24 to the cage 22. To couple the anchor 24 and the cage 22, the surface 92 engages the sidewalls of opening 62, and the latching surface 94 engages a cage surface 96 (FIG. 6) when the anchor 24 is moved to the deployed or second position.

Figure 6:
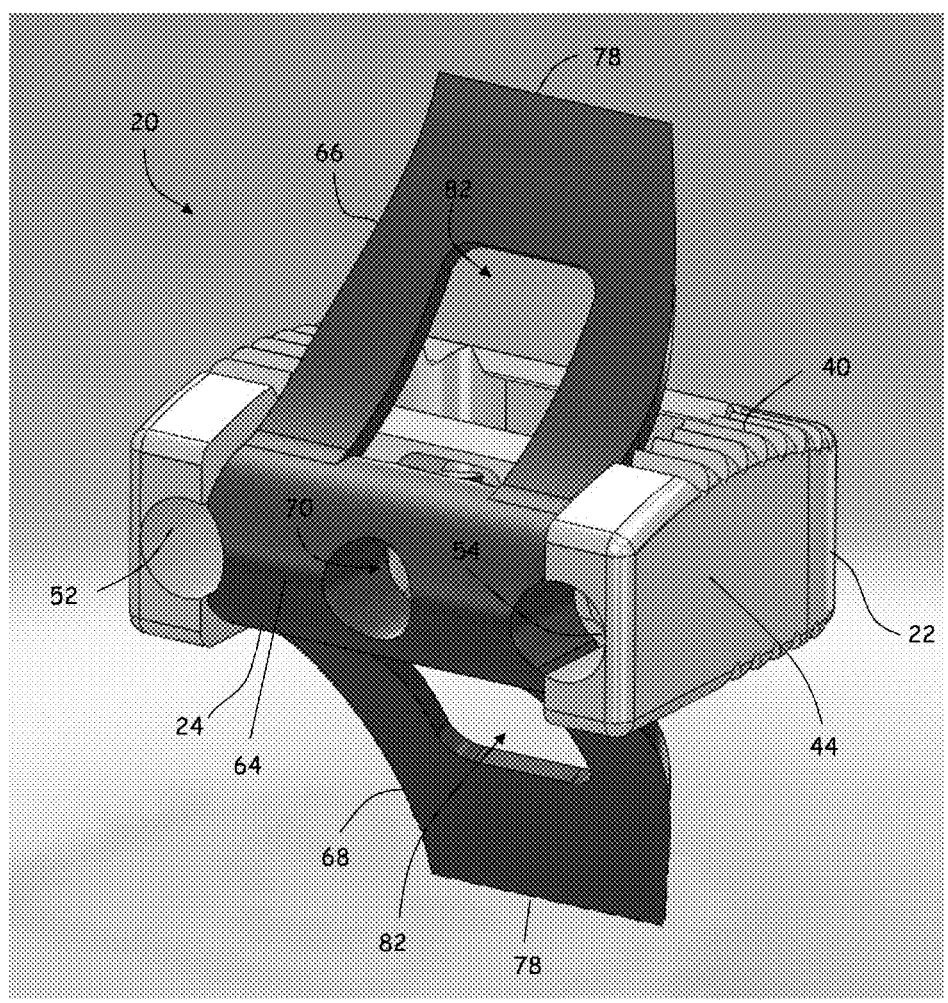
FIG. 6 is a perspective view of the spinal interbody device of FIG. 5 with the anchor in a second or deployed position.
Figure 7:
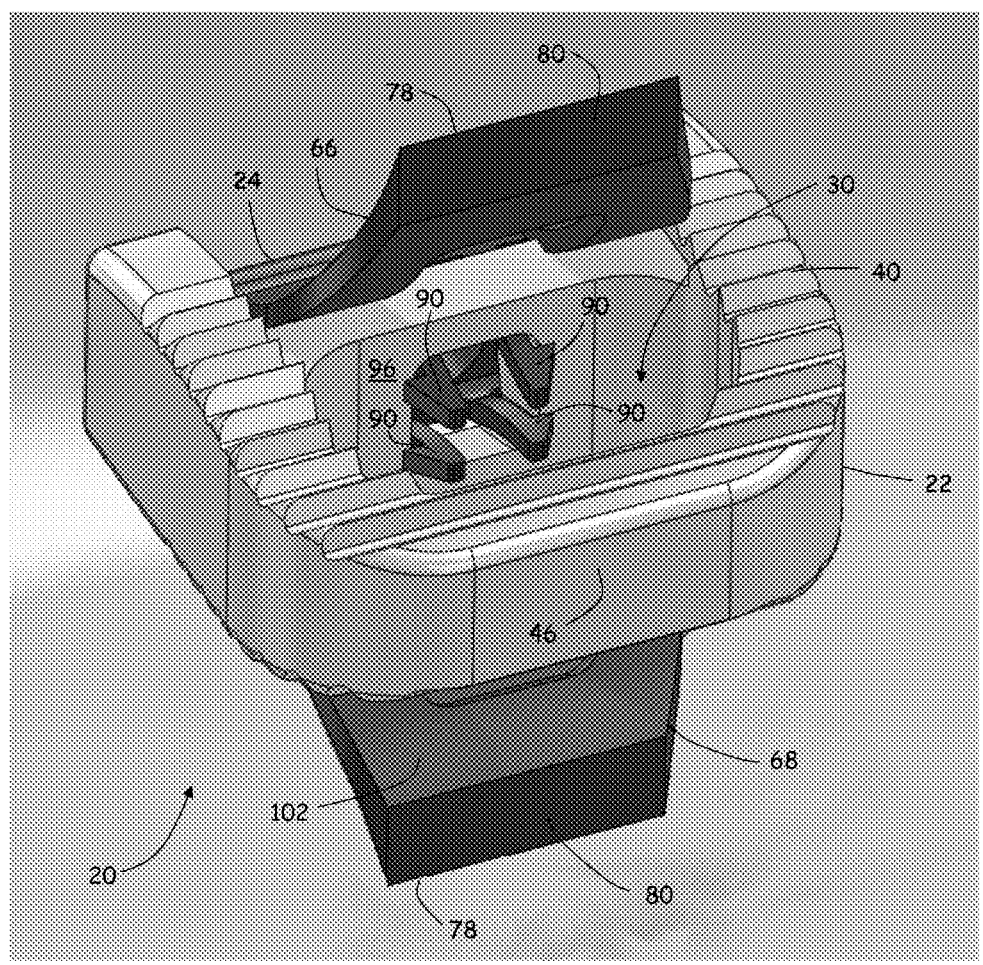
FIG. 7 is another perspective view of the spinal interbody device of FIG. 6.
Figure 8:
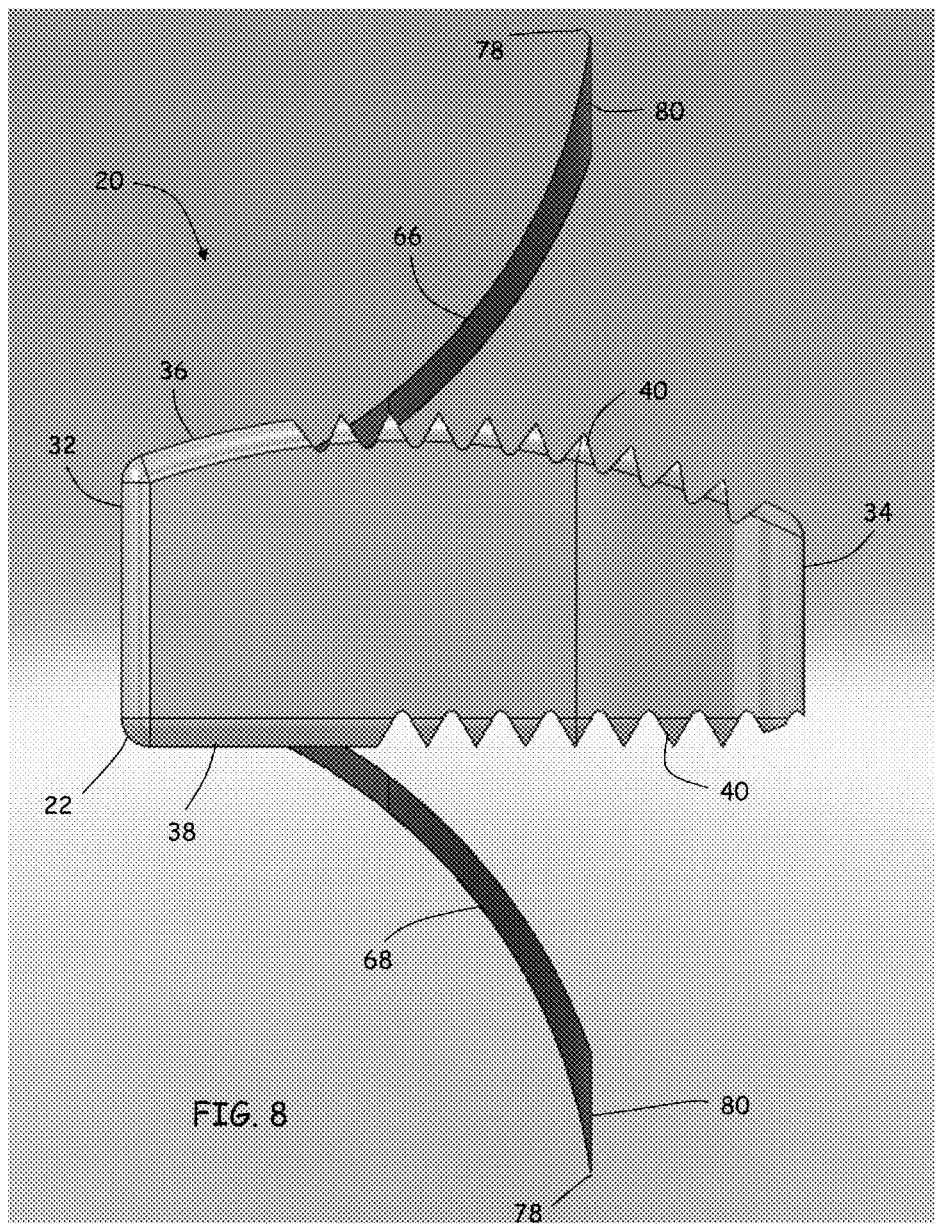
FIG. 8 is a side view of the spinal interbody device of FIG. 6.

The anchor 24 and cage 22 are configured to interlock together when inserted into position providing a means for securing the device 20 and its components to the adjacent vertebrae. The anchor 24 is slidably movable with respect to the cage 22 as shown in FIGS. 5-8. In general, the anchor 24 and cage 22 are arranged in a co-linear fashion with the arms 84, 86 aligned with the opening 62. The anchor 24 starts in a first position (FIG. 5) with the edge 78 and the surface 80 of each blade 66, 68 being positioned adjacent the ramp surfaces 58, 60. As the anchor 24 is moved from the first position, the surface 80 and the bottom surface 102 of the blades 66, 68 slide along the surfaces 58, 60 respectively to the deployed or second position (FIGS. 6-8). In the second position, the blades 66, 68 extend past the contact surfaces 36, 38.

It should be appreciated that when the anchor 24 is made from a material, such as titanium for example, that has a defined stress-strain curve with an elastic range and a plastic range, this deflection movement of the blade 66, 68 may plastically deform the blades 66, 68. As used herein, elastic deformation means that the stress on the material does not exceed the materials elastic limit, therefore the article may be repeatedly deformed and the article will return to its original shape. Once the elastic limit is exceeded, however, the material plastically deforms and the article does not return to its original shape. In one embodiment, the blades 66, 68 are arranged to plastically deform as anchor 24 is moved from the first position to the second position. By plastically deforming the blades 66, 68, advantages are gained in obviating the need for a locking arrangement, such as serrated teeth for example, to secure the anchor 24 to the adjacent vertebrae.

In addition to the deflection of the blades 66, 68, as the anchor 24 moves from the first position to the second position, the head portion 90 remains relatively undeformed since it does not contact the surface 58, 60. Rather, the head portion 90 enters the opening 62. As the anchor continues to move towards the second position, the angled surface 92 contacts the sidewall 104 of opening 62. The continued movement causes the arms 84, 86 to deflect, substantially in plane, until the latching surface 94 extends past the cage surface 96. At this point, the elasticity of the arms 84, 86 causes the arms to deflect back allowing the latching surface 94 to engage the cage surface 96 (FIG. 7). It should be appreciated that when the surfaces 94, 96 are engaged, the anchor 24 is secured to the cage 22 and the anchor will not move towards the first position under normal operating conditions.

It should be appreciated that while the blades 66, 68 are shown as having a curvature along the entire length of the blade, this is for exemplary purposes and the claimed invention should not be so limited. In other embodiments, the blades 66, 68 may be straight (e.g. parallel to the centerline 76) and have a curved distal end. In this embodiment, the center portion 48 may have a single surface that engages the blades rather than a pair of surfaces 58, 60.

It should be further appreciated that while the locking means is described with respect to the arms 84, 86, other means for coupling the anchor to the cage may also be used. In one embodiment, a threaded fastener may be inserted into opening 70 and engage a threaded opening 62 in the center portion 48.

Referring now to FIGS. 9-11, an embodiment of a surgical tool 56 is shown for use with a spinal interbody device 20. The tool 56 includes a housing 104 having an opening 110 sized to receive the anchor 24. The housing 104 includes openings in an opposite end sized to receive rods 100. The rods 100 are sized to fit within the openings formed by the slots 72 and opening 52 of device 20. The rods 100 may have a threaded end that allows the rods 100 to couple with the cage 22 within the openings 52 and slots 72. The housing 104 also includes an opening for a pusher rod 106. The pusher rod 106 may have a threaded end sized to couple with the threaded opening 70 of the anchor 24. The housing 104 may also have a notched area 108 that receives the anterior side 32 of the cage 22. The rods 100 and pusher rod 106 are coupled to slide relative to the housing 104.

When in the first position, the anchor 24 is at least partially within the opening 110. Once the surgeon has properly prepared the patient to receive the device 20, the tool 56 may be used to position the cage 22 in the desired location in between the vertebrae. Once the cage 22 is positioned, the pusher rod 106 is actuated to linearly slide the anchor 24 from the opening 110 and deployed towards the second position. In one embodiment, the pusher rod 106 may have a step 112 that can act as a positive stop against the housing 104 when the anchor 24 is in the second position. As the anchor 24 is moved, the blades 66, 68 deflect and the latching surfaces 94 engage to couple the anchor 24 to the cage 22 and the device 20 to the adjacent vertebrae 26, 28 (FIG. 21).

With the anchor 24 secured to the cage 22, the surgeon may then uncouple the pusher rod 106 from the threaded opening 70. Thereafter, the rods 100 may be uncoupled from the cage 22 allowing the tool 56 to be removed from the patient with the device 20 in place. In some circumstances, the surgeon may desire to remove or reposition the device 20. In this circumstance, the surgeon may reattach the tool 56 to the device 20 by coupling the rods 100 to the cage 22 and the pusher rod 106 to the anchor 24. With the tool 56 and the device 20 coupled, the surgeon may then actuate (e.g. pull) the pusher rod 106 away from the patients spine with sufficient force to cause the arms 84, 86 to deflect and disengage the latching surface 94 from the cage surface 96. Thus the insertion of device 20 is reversible without having to resort to any cutting or machining of material from the device 20 within the patient.

It should be appreciated that while this embodiment illustrates a single surgical tool 56, in other embodiments, multiple surgical tools may be used for insertion, deployment, retraction, and/or removal. Further, it should be appreciated that the rods 100 and pusher rod 106 may be actuated by any suitable mechanism, including but not limited to a rotatable knobs, electrical motors, spring-loaded mechanisms and the like.

Referring now to FIGS. 12-20, another embodiment of a spinal interbody device 20 is shown having a two piece cage 114. The cage 114 includes a posterior member 116 and an anterior member 118. The posterior member 116 may be constructed of various biocompatible materials including, but not limited to titanium or a polymer such as polyetheretherkentone (PEEK) for example. The posterior member 116 may generally taper from the interface with the anterior member 118 to a posterior side 120. The posterior member 116 may also have a curved top contact surface 122 and a substantially flat bottom contact surface 124. The surfaces 122, 124 may include a plurality of optional teeth or grooves 127 that engage the adjacent superior and inferior vertebrae to assist in maintaining the spinal interbody device 20 in place.

It should be appreciated that the curvature, taper, or angle between the contact surfaces 122, 124 may be varied to match the patient anatomy. The height, or distance between the contact surfaces 122, 124 may also be changed to match the patient anatomy. Further, while the contact surfaces 122, 124 are illustrated as being substantially flat on one side and curved on the other, other profiles may be used, including but not limited to parallel, tapered, concave or convex surfaces for example. Additionally, the posterior member may be substantially semi-cylindrical in shape.

The posterior member 116 forms a generally U-shaped body having an edge portion 126 along the posterior side 120 and a pair of arms 128 that extend to couple with the anterior member 118. The posterior member 116 and anterior member 118 cooperate to define an opening 130. In one embodiment, the posterior member 116 is a solid member without an opening 130. In the exemplary embodiment, the posterior member 116 includes a slot 132 that is sized to receive a projection 134 on the anterior member 118. The anterior member 118 may be coupled to the posterior member 116 by any suitable means, such as a press fit, adhesive or a mechanical fastener. As discussed above, the opening 130 may be filled with an autograft or other biocompatible material to facilitate fusion of the vertebrae.

The anterior member 118 may have a generally H-shaped body with a center portion 136 and a pair of anterior arms 138. In the exemplary embodiment, the anterior member 118 is made from a bio-compatible metal material such as but not limited to titanium. As discussed above, in one embodiment, the anterior member 118 may have a pair of posterior projections 134 that engage slots 132 in the arms 128 to couple the posterior member 116 and the anterior member 118. It should be appreciated that the anterior member 118 and the posterior member 116 may be coupled to each other using a variety of means, including but not limited to press-fit, bonding, mechanical fastening, and insert molding for example.

Each of the anterior arms 138 includes an opening 140, 142 adjacent an open side 144. The openings 140, 142 may include threaded portions that allow the cage 114 to be coupled with the tool 156. Adjacent the openings 140, 142, the anterior member 118 has pairs of projections 146, 148 on the ends of the arms 138 that extend parallel to the center portion 136. As will be discussed in more detail below, the projections 146, 148 assist in fixing the anchor in place after deployment of the anchor.

The center portion 136 includes a first surface 147 and a second surface 149 separated by a planar surface 151. As will be discussed in more detail below, the surfaces 147, 149 are curved such that as the blade of the anchor contacts the surfaces 147, 149 the blades are deflected into the adjacent vertebrae. In one embodiment, the surfaces 147, 149 are mirror images of each other on opposing sides of a horizontal plane. In another embodiment, the surfaces 147, 149 are planar surfaces disposed on an angle.

In one embodiment, the posterior member 116 defines the four sides of the opening 130 and the anterior member 118 couples to the side of the posterior member 116 adjacent the opening 130. In another embodiment, the opening 130 is a circular, oval, elliptical or other shape having a continuous curved surface that is defined by the posterior member 116, the anterior member 118 or a combination of both.

Figure 15:
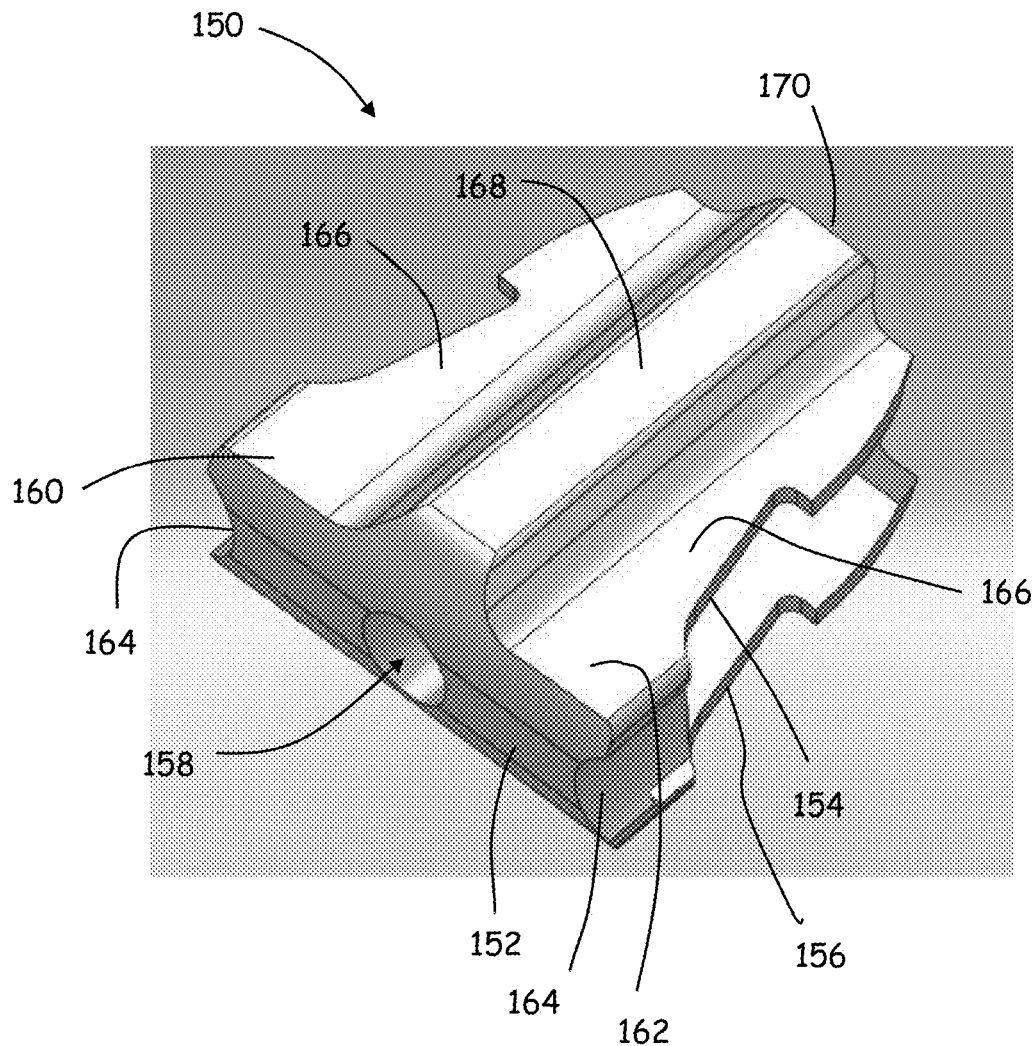
FIG. 15 is a perspective view of an anchor for use with the cage of FIG. 12.
Figure 16:
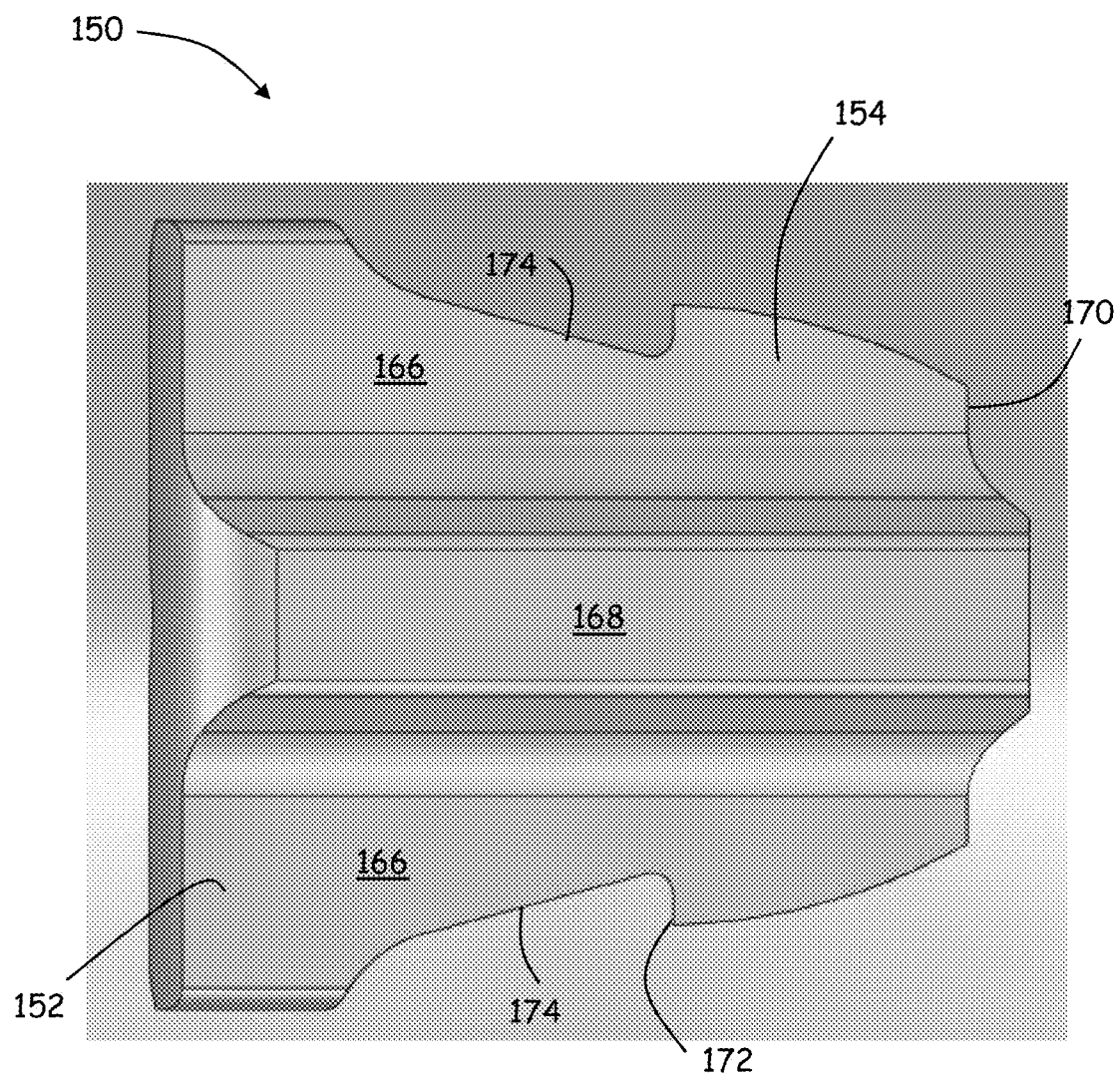
FIG. 16 is a top view of the anchor of FIG. 15.
Figure 17:
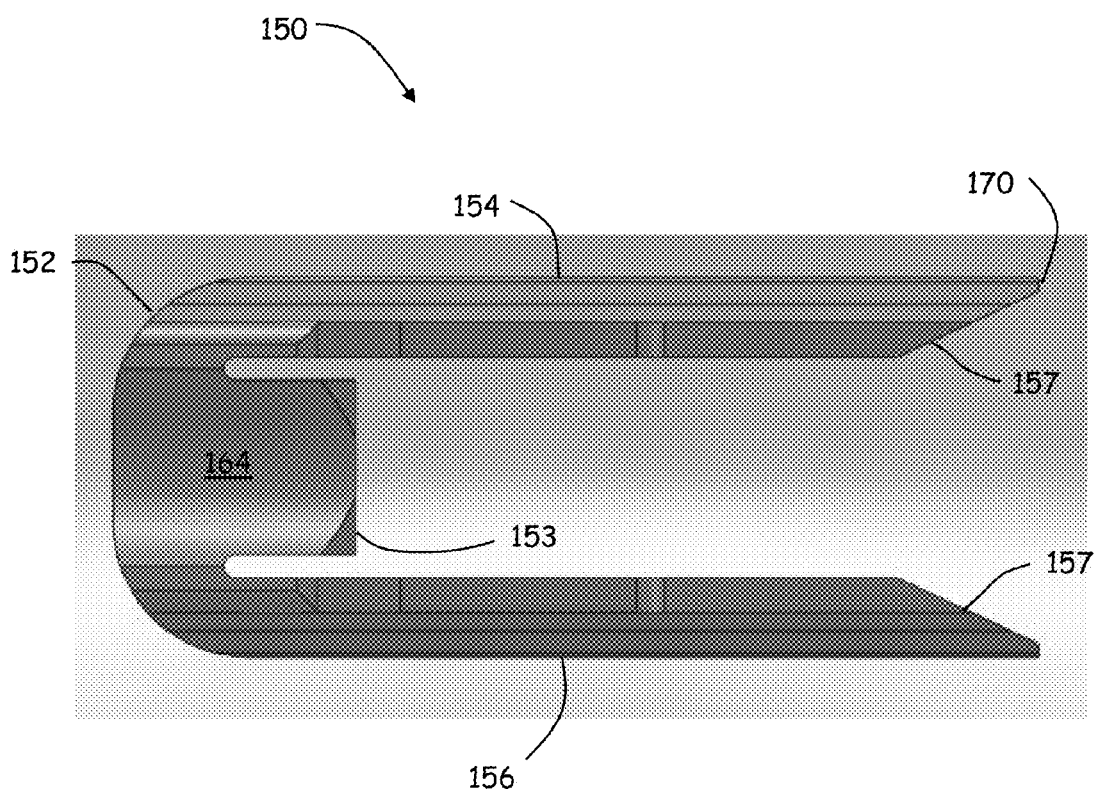
FIG. 17 is a side view of the anchor of FIG. 15.

An exemplary anchor 150 is shown in FIGS. 15-17. The anchor 150 includes a body 152. A first blade 154 and a second blade 156 extend from opposing sides of the body 152. The anchor 150 may be made from a metal such as stainless steel or titanium for example. The body 152 may include a threaded opening 158 located centrally along the width of the body 152. The threaded opening may be configured to releasably couple with a tool, such as pusher rod 106 for example. The body 152 is sized to fit within the open side 144 with the end portions 160, 162 and has a height sized to fit between the projections 146, 148 respectively. The ends 160, 162 include a semi-circular surfaces 164 that are sized to allow the rods 100 of tool 56 to extend past the anchor 150 and engage the cage 114.

In one embodiment, the body 152 may include a surface 153 disposed on an opposite side from the opening 158 disposed between the blades 154, 156. The surface 153 is arranged to contact the planar surface 151 to provide a stop surface that prevents further insertion of the anchor 150 into the cage 114.

In the exemplary embodiment, the blades 154, 156 are mirror images of each other. Each blade 154, 156 includes a generally planar surface 166 and a rib portion 168. The planar surface 166 has a profile (FIG. 16) such that the distal end 170 widens as the blade 154, 156 extends toward the body 152 until reaching edge 172. At edge 172, the blade 154, 156 steps inward, decreases in width and then tapering outward along surface 174 until reaching the body 152. As will be discussed in more detail below, the step formed at edge 172 decreases the width of the blade 154, 156 to be less than the distance between the projections 146 for the blade 154 and also less than the distance between the projections 148 for blade 156. In other words, the portion of the blade 154, 156 adjacent surface 174 will not pass between the respective projections 146, 148 until the body 152 is substantially positioned within the open side 144 (See FIG. 20). This provides advantages in allowing the surgeon to easily retract the blade 154, 156 prior to full insertion. By changing the angle of the taper of surface 174, the fixation point (i.e. the point where the blade will not retract from the cage without a tool) for the blade 154, 156 may be altered. Further, the surface formed at edge 172 provides a resistance to retraction when inserted into the vertebrae.

It should be appreciated that in some embodiments, the blades 154, 156 are straight without a tooth portion or edge 172. In still other embodiments, the blades 154, 156 are tapered along the length from the distal end 170 to the body 152. In still other embodiments, the blade may include a serrated edge.

The rib 168 is sized to fit in between the projections 146, 148 such that when the anchor 150 is in the deployed position, the rib 168 will be disposed between the projections 146, 148. The thickness and width of the rib 168 may be altered to provide the desired amount of stiffness and resistance. Opposite the rib 168, the blades 154, 156 have a generally planar surface that tapers adjacent the distal end 170. The tapered surface 175 provides advantages in assisting the initial deflection of the blades and in penetrating the adjacent vertebrae.

It should be appreciated that while embodiments herein describe the anchor 150 having a rib 168 extending along the length of the blades 154, 156, in other embodiments, the blades 154, 156 have no rib but have a planar or curved surface. In still other embodiments, instead of a distinct rib, the blades 154, 156 may increase in thickness from the edge to the center portion of the blade.

Figure 18:
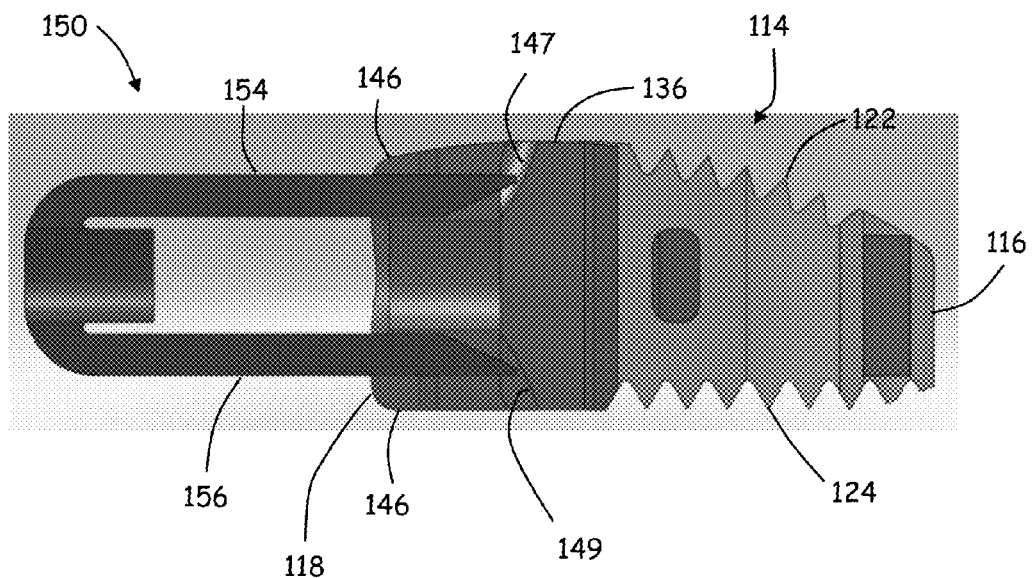
FIG. 18 is a side sectional view of the spinal interbody device with the anchor of FIG. 15 being inserted into the cage of FIG. 12.
Figure 19:
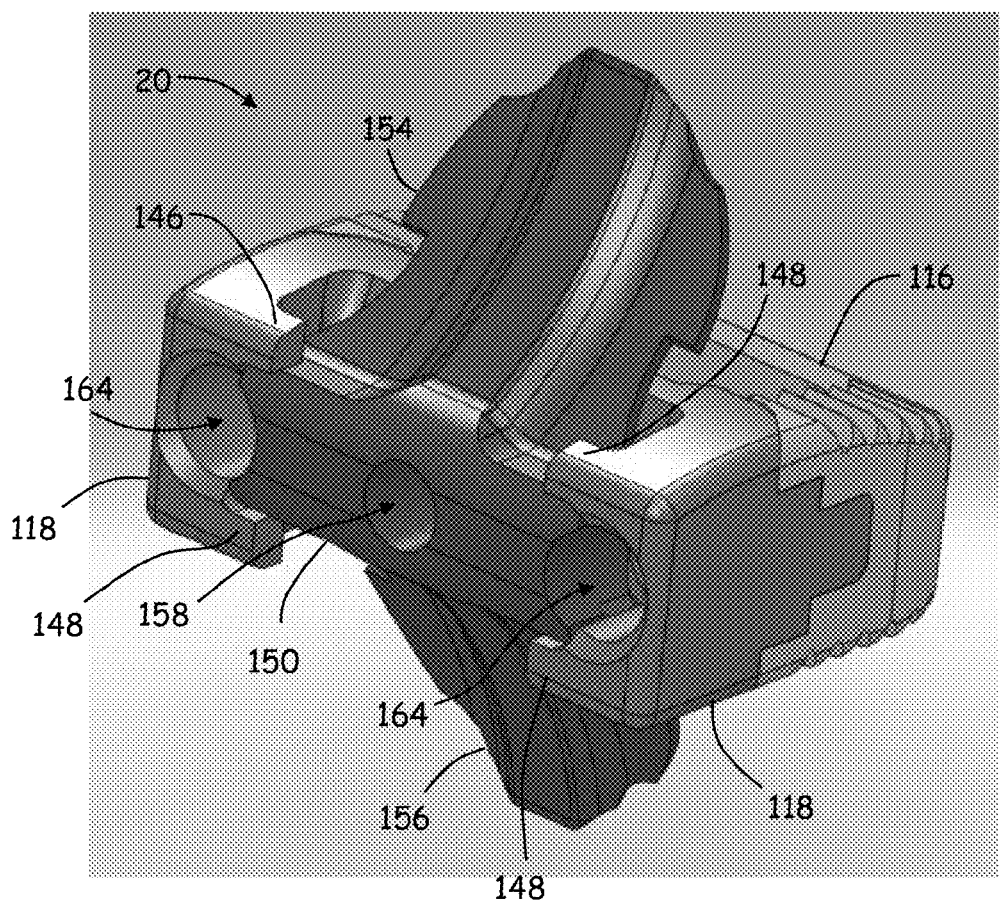
FIG. 19 is a perspective view of the spinal interbody device with the anchor of FIG. 15 fully inserted.
Figure 20:
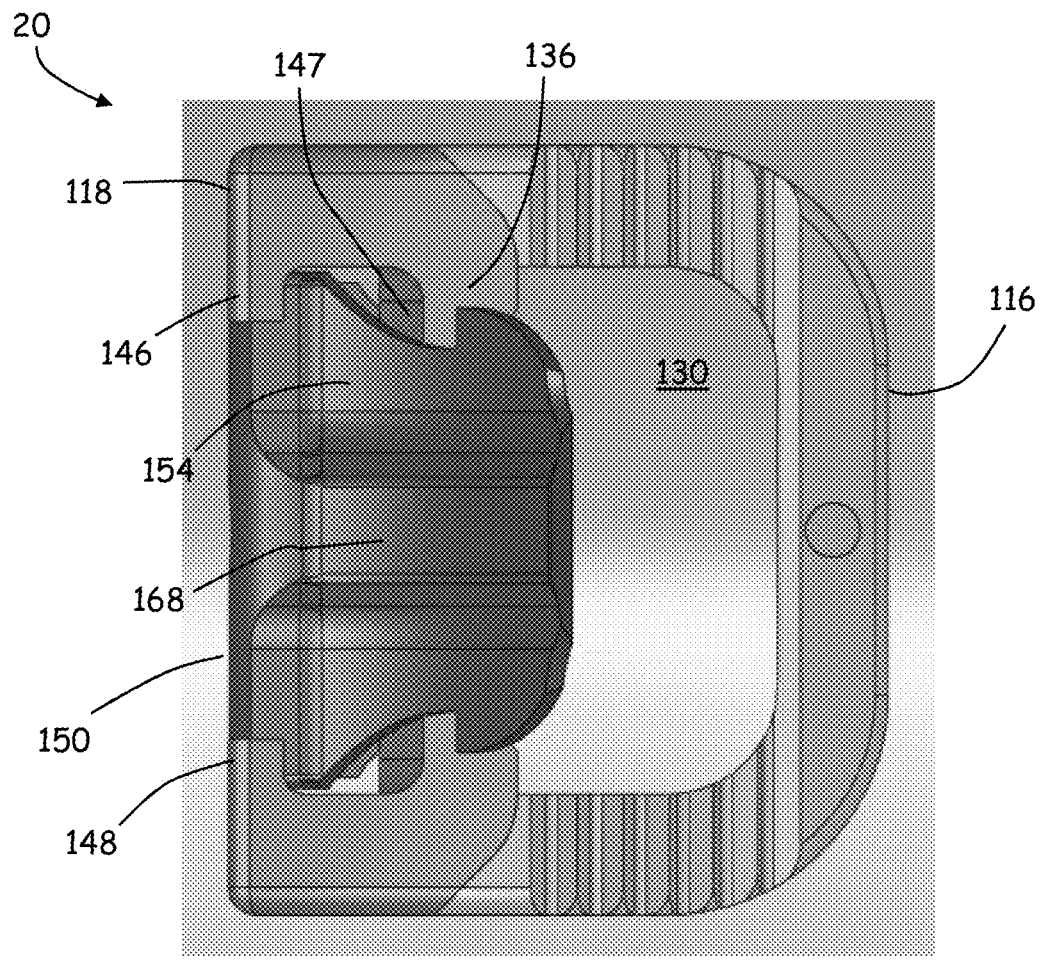
FIG. 20 is a top view of the spinal interbody device with the anchor of FIG. 15 fully inserted.

The anchor 150 is configured to be inserted through the open end 144 of cage 114 (FIG. 18). The blades 154, 156 extend past the projections 146, 148 until contacting the surfaces 147, 149. It should be appreciated that the distance between the blades 154, 156 is sufficient to allow the distal end 170 of each blade 154, 156 to contact the surfaces 147, 149 and not the planar surface 151. Once the blades 154, 156 contacts the surfaces 147, 149, further movement of the anchor 150 results in the blades 154, 156 deflecting to slide past the center portion 136 and into the adjacent vertebrae.

In the exemplary embodiment, the anchor 150 is made from a material, such as titanium for example, that has a defined stress-strain curve with an elastic range and a plastic range. As discussed above, once the elastic limit is exceeded, the material plastically deforms and does not return to its original shape. As the anchor 150 is moved against the center portion 136, the blades 154, 156 deform, bend or deflect. In the exemplary embodiment, this deflection continues causing a plastic deformation of the blades 154, 156 as the body 152 approaches and enters the open side 144. The plastic deformation of the blades 154, 156 provides advantages in retaining the anchor 150 and preventing movement in the reverse direction.

As discussed above, the anchor 150 and cage 114 are configured to interlock together when inserted into position by means of the projections 146, 148 and the surface 166 adjacent the body 152. Since the area of surface 166 adjacent the body 152 is wider than space between the projections 146, 148, the surface 166 will deflect into the space between the projections 146, 148 and the center portion 136. As a result, once the anchor 150 is inserted and the surface 166 is moved past the edge of the projections 146, 148, the anchor 150 will be interlocked with the cage 114. In this position, the anchor 150 will not translate or move laterally in the reverse direction without the assistance of a tool that can overcome the resistance of the plastic deformation in the blade. It should be appreciated that the point where the anchor 150 and cage 114 form an interlocking configuration may be changed by adjusting the shape of the blades 154, 156 to move the point where the surface 174 is wider than the space between the projections 146, 148.

It should be appreciated that the spinal interbody device 20 illustrated in FIGS. 12-20 may be inserted using a tool such as surgical tool 56 shown in FIGS. 9-11. The rods 100 are sized to fit within the openings 140, 142 and the surfaces 164. The pusher rod 106 couples with the opening 158. The cage 114 and anchor 150 are sized to cooperate with the housing 104 such that the anchor 150 is at least partially disposed within the housing 104 and the cage 114 is engaged with the end of the housing 104 during insertion.

It should be appreciated that while the blades 154, 156 are shown as having a curvature along the entire length of the blade, this is for exemplary purposes and the claimed invention should not be so limited. In other embodiments, the blades 154, 156 may be straight with a curved distal end. In this embodiment, the center portion 136 may have a single surface that engages the blades rather than a pair of surfaces 147, 149.

It should be further appreciated that while the locking means is described with respect to the blades 154, 156 being arranged between the projections 146, 148 and the center portion 136, other means for coupling the anchor to the cage may also be used. In one embodiment, a threaded fastener may be inserted into opening 158 and engage a threaded opening (not shown) in the center portion 136.

Figure 22:
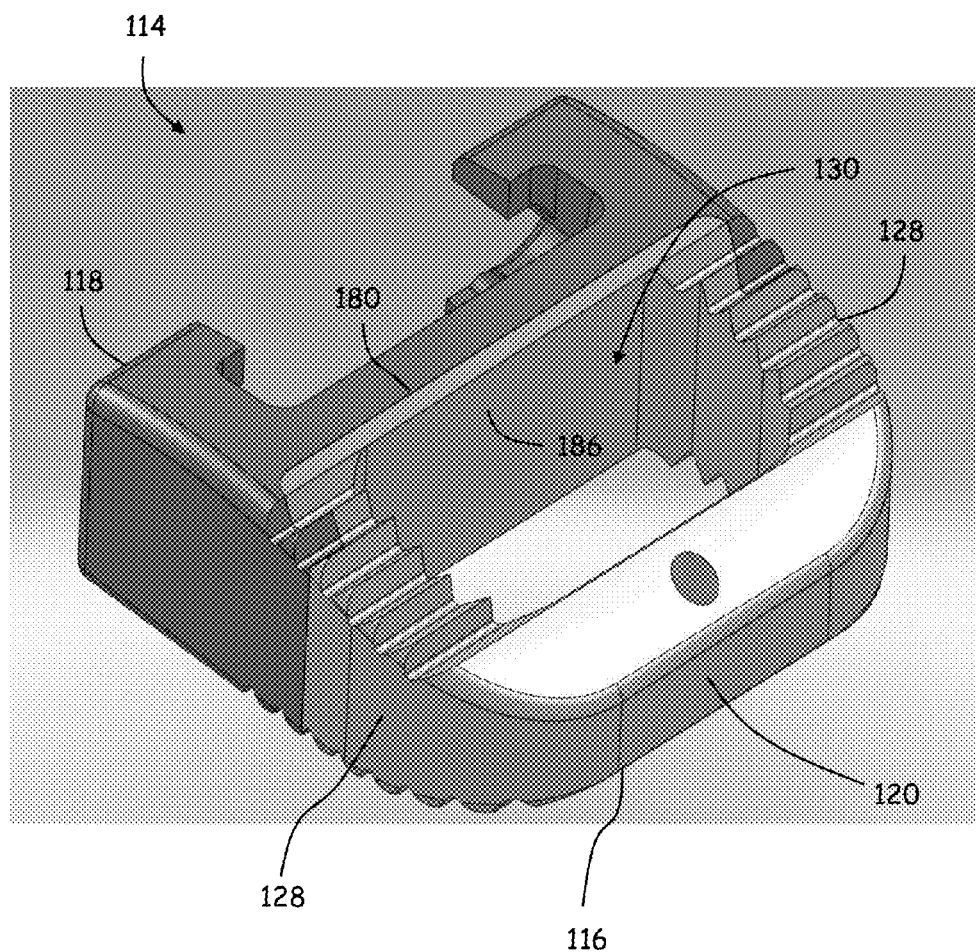
FIG. 22 is a perspective view of a cage for a spinal interbody device in accordance with another embodiment of the invention; and, FIG. 23 is a top view of the cage of FIG. 22.
Figure 23:
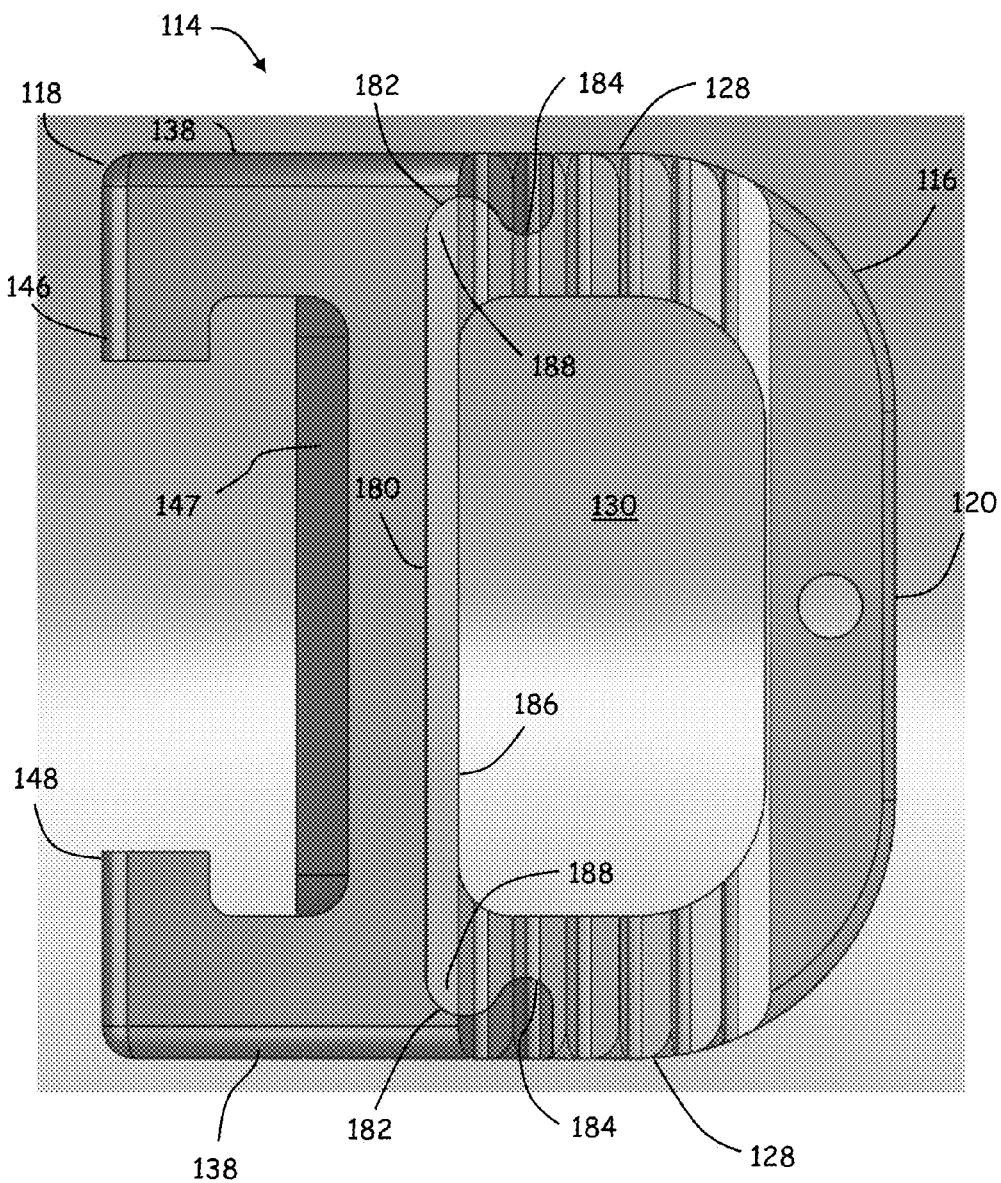

Referring now to FIGS. 22 and 23 another embodiment of cage 114 is shown having the posterior member 116 coupled to the anterior member 118. In this embodiment, the anterior member 118 includes a slot 180 that extends along a side opposite the surfaces 147, 149. The slot 180 includes a lower stop surface (not shown) on the inferior side of the cage 114. In one embodiment, the slot 180 includes curved surfaces 182, 184 that define an S-shaped surface on each end of the slot.

The posterior member 116 includes a wall 186 opposite the posterior side 120. The wall 186 cooperates with the posterior side 120 and the arms 128 to define the opening 130. The ends 188 of the wall 186 are curved to substantially match the surfaces 182, 184 of the slot 180. To assemble the cage 114, the wall 186 is aligned with the slot 180 and slid into the slot 180 until the bottom of the wall engages the stop surface at the bottom of the slot 180. In one embodiment, there is a small interference fit between the wall 186 and the slot 180 and the posterior member 116 is coupled to the anterior member 118 by a press fit.

The spinal interbody device 20 provides advantages that include the rigid fixation of the stand-alone implant. The spinal interbody device 20 provides additional advantages in resisting motion typically seen in the spinal column such as lateral bending, torsion and extension. The rigidity afforded by this spinal interbody device 20 fixes the adjacent superior and inferior vertebral bodies together allowing for a fusion to occur across the spinal segment. The spinal interbody device 20 provides additional advantages in that the anchor may be moved in both directions to allow deployment, removal, or repositioning. The spinal interbody device 20 also provides advantages in that a single surgical tool may be used to insert, deploy, and remove the implant. The spinal interbody device 20 provides further advantages in that it may be used from an anterior, a lateral or a posterior direction. The spinal interbody device 20 provides further advantages in that it may be used in cervical or lumbar procedures.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A spinal interbody device comprising:
a cage having a center portion with a first surface and an opposing second surface, the cage further including a first arm and a second arm extending from the center portion the first arm having a pair of first projections and the second arm having a pair of second projections, the pair of first projections and the pair of second projections being disposed on opposing sides of an open side;
an anchor having a first blade and a second blade movable between a first position and a second position, the first blade and second blade disposed to engage the first surface and the second surface and plastically deform as the anchor is moved from the first position to the second position, wherein the first blade is at least partially disposed between one of the pair of first projections and the center portion and the second blade being at least partially disposed between the other of the pair of first projections and the center portion when the anchor is in the second position.

2. The device of claim 1 wherein:
the anchor is sized to be received in the open side; and,
a locking means formed by at least partially disposing the at least one blade between at least one of the pair of first projections and the center portion when the anchor is in the second position.

3. The device of claim 2 wherein the first blade is at least partially disposed between one of the pair of second projections and the center portion and the second blade is at least partially disposed between the other of the pair of second projections and the center portion when the anchor is in the second position.

4. The device of claim 2 wherein the first surface and the second surface are curved.

5. The device of claim 2 wherein the first arm includes a first opening disposed on an end and the second arm includes a second opening disposed on an end.

6. The device of claim 1 wherein the cage includes a posterior member coupled to the center portion.

7. A spinal interbody device comprising:
a cage having a first member coupled to a second member, the first member having a center portion with a first arm and a second arm extending from opposing ends, the center portion further having a first surface and a second surface, the first arm having at least one first projection on an end opposite the center portion and the second arm having at least one second projection an end opposite the center portion, the first arm and the second arm defining an open side; and,
an anchor having a body with a first blade and a second blade extending from one side, the anchor being movable between a first position and a second position, the first blade being disposed to contact the first surface and the second blade disposed to contact the second surface when the anchor is moved from the first position to the second position, the first blade and the second blade plastically deforming as the first blade and second blade move from the first position to the second position, and wherein first blade is at least partially disposed between the at least one first projection and the at least one second projection and the center portion when the anchor is in the second position.

8. The device of claim 7 further comprising a plurality of first grooves formed in a first contact surface disposed on one side of the cage and a second plurality of grooves formed in a second contact surface on an opposing side of the cage.

9. The device of claim 7 wherein the first member and the second member are coupled by a press fit.

10. The device of claim 7 wherein the at least one blade includes a first portion having a distal end and a second portion having an end adjacent the body, the first portion tapering from a first width to a second width as the first portion extends from the distal end towards the body, the second width being larger than the first width, and the second portion having a third width adjacent the first portion, the second width being larger than the third width.

11. The device of claim 7 wherein the at least one blade includes a rib portion extending from the body to a distal end.

12. The device of claim 7 wherein:
the body includes a pair of semi-circular surfaces disposed on opposing ends of the body;
the first arm includes a first opening on an end opposite the center portion;
the second arm includes a second opening on an end opposite the center portion; and,
the pair of semi-circular surfaces being disposed substantially co-axial with the first opening the second opening when then the anchor is in the second position.

13. The device of claim 1 wherein the anchor is arranged to move between the second position and the first position.

14. The device of claim 7 wherein the anchor is arranged to move between the second position and the first position.

* * * * *